US00PP34432P2

(12) United States Plant Patent
Spil

(10) Patent No.: US PP34,432 P2
(45) Date of Patent: Jul. 19, 2022

(54) ***ECHINACEA* PLANT NAMED 'IFECSSPUR'**

(50) Latin Name: *Echinacea hybrida*
Varietal Denomination: 'IFECSSPUR'

(71) Applicant: INNOFLORA PLANT BREEDING B.V., Heerhugowaard (NL)

(72) Inventor: Glenn Spil, Zuidermeer (NL)

(73) Assignee: INNOFLORA PLANT BREEDING B.V., Heerhugowaard (NL)

( * ) Notice: Subject to any disclaimer, the term of this patent is extended or adjusted under 35 U.S.C. 154(b) by 0 days.

(21) Appl. No.: 17/563,990

(22) Filed: Dec. 28, 2021

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Echinacea* plant named 'IFECSSPUR', characterized by its upright and relatively compact plant habit; moderately vigorous to vigorous growth habit; freely branching habit; strong flowering stems that are purplish red in color; numerous and large single-type inflorescences with purplish red-colored ray florets and red-colored receptacle spines; and good garden performance.

1 Drawing Sheet

Botanical designation: *Echinacea hybrida.*
Cultivar denomination: 'IFECSSPUR'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Innoflora Plant Breeding B.V. of Heerhugowaard, The Netherlands on Nov. 26, 2021, application number 2021/3057. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Echinacea* plant, botanically known as *Echinacea hybrida*, and hereinafter referred to by the name 'IFECSSPUR'.

The new *Echinacea* plant is a product of a planned breeding program conducted by the Inventor in Heerhugowaard, The Netherlands. The objective of the breeding program is to develop new vigorous and freely flowering *Echinacea* plants with large inflorescences with unique and attractive ray floret coloration.

The new *Echinacea* plant originated from a cross-pollination in July, 2017 in Heerhugowaard, The Netherlands of a proprietary selection of *Echinacea hybrida* identified as code number 009-15-K012-02, not patented, as the female, or seed, parent with a proprietary selection of *Echinacea hybrida* identified as code number 009-13-K058-01, not patented, as the male, or pollen, parent. The new *Echinacea* plant was discovered and selected by the Inventor as a single flowering plant from within the progeny of the stated cross-pollination grown in a controlled greenhouse environment in Heerhugowaard, The Netherlands in September, 2018.

Asexual reproduction of the new *Echinacea* plant by in vitro meristem culture in a controlled environment in Heerhugowaard, The Netherlands since August, 2019 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'IFECSSPUR'. These characteristics in combination distinguish 'IFECSSPUR' as a new and distinct *Echinacea* plant:

1. Upright and relatively compact plant habit.
2. Moderately vigorous to vigorous growth habit.
3. Freely branching habit.
4. Strong flowering stems that are purplish red in color.

5. Numerous and large single-type inflorescences with purplish red-colored ray florets and red-colored receptacle spines.
6. Good garden performance.

Plants of the new *Echinacea* can be compared to plants of the female parent selection. Plants of the new *Echinacea* differ primarily from plants of the female parent selection in the following characteristics:

1. Plants of the new *Echinacea* are more compact than plants of the female parent selection.
2. Plants of the new *Echinacea* and the female parent selection differ in ray floret color as plants of the new *Echinacea* have purplish red-colored ray florets whereas plants of the female parent selection have orange red-colored ray florets.

Plants of the new *Echinacea* can be compared to plants of the male parent selection. Plants of the new *Echinacea* differ primarily from plants of the male parent selection in the following characteristics:

1. Plants of the new *Echinacea* and the male parent selection differ in ray floret color as plants of the new *Echinacea* have purplish red-colored ray florets whereas plants of the male parent selection have orange red-colored ray florets.
2. Peduncles of plants of the new *Echinacea* are purplish red in color whereas peduncles of plants of the male parent selection are green in color.

Plants of the new *Echinacea* can be compared to plants of *Echinacea purpurea* 'Hilmoocour', disclosed in U.S. Plant Pat. No. 32,869. In side-by-side comparisons, plants of the new *Echinacea* differ primarily from plants of 'Hilmoocour' in the following characteristics:

1. Plants of the new *Echinacea* have larger inflorescences with more ray florets than plants of 'Hilmoocour'.
2. Plants of the new *Echinacea* have more intense purplish red-colored ray florets than plants of 'Hilmoocour'.

BRIEF DESCRIPTION OF THE PHOTOGRAPH

The accompanying photograph illustrates the overall appearance of the new *Echinacea* plant showing the colors as true as it is reasonably possible to obtain in colored reproductions of this type. Colors in the photograph may differ slightly from the color values cited in the detailed botanical description which accurately describe the colors of the new *Echinacea* plant.

The photograph is a side perspective view of a typical flowering plant of 'IFECSSPUR' grown in a container.

DETAILED BOTANICAL DESCRIPTION

The aforementioned photograph and following observations and measurements describe plants grown during the late summer in 17-cm containers in an outdoor nursery in Heerhugowaard, The Netherlands and under cultural practices typically used in commercial *Echinacea* production. During the production of the plants, day temperatures ranged from 16° C. to 30° C. and night temperatures ranged from 8° C. to 18° C. Plants were pinched eight weeks after planting and were 19 weeks old when the photograph and description were taken. In the following description, color references are made to The Royal Horticultural Society Colour Chart, 2015 Edition, except where general terms of ordinary dictionary significance are used.

Botanical classification: *Echinacea hybrida* 'IFECSSPUR'.

Parentage:

*Female parent*.—Proprietary selection of *Echinacea hybrida* identified as code number 009-15-K012-02, not patented.

*Male parent*.—Proprietary selection of *Echinacea hybrida* identified as code number 009-13-K058-01, not patented.

Propagation:

*Type*.—By in vitro meristem culture.

*Time to initiate roots, summer*.—About twelve days at temperatures about 20° C.

*Time to initiate roots, winter*.—About 16 days at temperatures about 20° C.

*Time to produce a rooted young plant, summer*.—About 36 days at temperatures about 18° C.

*Time to produce a rooted young plant, winter*.—About 42 days at temperatures about 18° C.

*Root description*.—Thick, fleshy; typically white in color, actual color of the roots is dependent on substrate composition, water quality, fertilizer type and formulation, substrate temperature and physiological age of roots.

*Rooting habit*.—Moderately freely branching; sparse.

Plant description:

*Plant form and growth habit*.—Herbaceous perennial; upright and relatively compact plant habit, inverted triangle; freely basal branching habit with about nine primary lateral branches developing per plant; moderately vigorous to vigorous growth habit and moderate growth rate.

*Plant height*.—About 48.5 cm.

*Plant diameter or spread*.—About 47.5 cm.

*Lateral branches*.—Length: About 27.3 cm. Diameter: About 6 mm. Internode length: About 2.9 cm. Aspect: Erect to about 20° from vertical. Strength: Strong. Texture: Moderately pubescent; strigose, rough; with subsequent development becoming glabrous. Color: Close to a blend of 183A and N186C and proximally, close to 152B.

Leaf description:

*Basal and cauline leaves*.—Arrangement: Alternate, simple. Length: About 13.4 cm. Width: About 4.5 cm. Shape: Narrowly ovate. Apex: Narrowly acute. Base: Attenuate. Margin: Coarsely and shallowly dentate to serrate. Texture and luster, upper and lower surfaces: Moderately pubescent, strigose and rough; slightly glossy. Venation pattern: Pinnate. Color: Developing leaves, upper surface: Darker than 143A. Developing leaves, lower surface: Close to a blend of 146B and 147B. Fully expanded leaves, upper surface: Close to NN137A to slightly darker than NN137A; venation, close to 144A. Fully expanded leaves, lower surface: Close to 137B; venation, close to 146D.

*Petioles, basal and cauline leaves*.—Length: About 5.5 cm. Diameter: About 2.25 mm by 3 mm. Texture, upper surface: Smooth, glabrous; margins, sparsely to moderately pubescent. Texture, lower surface: Sparsely pubescent. Color, upper surface: Close to NN137A; midvein, close to 152A; basal leaves, proximally, tinged with close to 176D. Color, lower surface: Close to N138B; midvein, close to 146C.

Inflorescence description:

*Appearance*.—Large single-type inflorescences with ray and disc florets arranged on a capitulum; inflorescences positioned upright above the foliar plane on mostly upright and strong peduncles.

*Flowering habit*.—Freely flowering habit with about 40 developing and fully developed inflorescences per plant.

*Fragrance*.—Moderately fragrant; sweet and pleasant.

*Time to flower*.—Plants flower continuously from early July to late September in The Netherlands.

*Inflorescence longevity*.—Inflorescences maintain good substance for about three weeks on the plant; inflorescences persistent.

*Inflorescence buds*.—Height: About 2.1 cm. Diameter: About 3.5 cm. Shape: Flattened globular. Color: Close to 187A.

*Inflorescence size*.—Diameter: About 10.9 cm. Depth (height): About 2.4 cm. Disc diameter: About 3.3 cm.

*Receptacles*.—Height: About 1 cm. Diameter: About 1 cm. Shape: Broadly ovate. Color: Close to NN155A.

*Ray florets*.—Quantity and arrangement: About 20 to 30 arranged in a single whorl at the base of the receptacle. Length: About 4.6 cm. Width: About 1.4 cm. Shape: Narrowly elliptic; moderately carinate. Apex: Emarginate to praemorse. Base: Cuneate. Margin: Entire. Texture and luster, upper surface: Smooth, glabrous; velvety; matte. Texture and luster, lower surface: Sparsely pubescent; slightly glossy. Aspect: About 95° from vertical to horizontal. Color: When opening, upper surface: Close to a blend of 60D and 61B. When opening, lower surface: Close to 59C. Fully opened, upper surface: Close to 61B and at the base, close to 60B; venation, similar to lamina; color becoming closer to 60C and 60D with subsequent development. Fully opened, lower surface: Close to 59C and 60B; venation, similar to lamina; color becoming closer to 59D with subsequent development.

*Disc florets*.—Quantity and arrangement: About 260 per inflorescence, arranged spirally at the center of the inflorescence. Length: About 1.1 cm. Diameter: About 4 mm. Shape: Tubular; proximally, 10% free, not fused. Apex: Acute. Base: Fused. Margin, free-part: Entire. Texture and luster, inner and outer surfaces: Smooth, glabrous; moderately glossy. Color, when opening, inner surface: Apex: Close to 181A to 181B. Mid-section: Close to 152C. Base: Close to 144B. Color, when opening, outer surface: Apex: Close to 182D. Mid-section: Close to 152C. Base: Close to 144B. Color, fully opened, inner and outer surfaces: Apex and mid-section: Close to 153D; margins of free lobes, close to 185A. Base: Close to 144B.

*Receptacle spines*.—Quantity: One per disc floret; about 260 per inflorescence. Shape: Acicular. Apex: Acute. Base: Attenuate. Texture and luster: Smooth, glabrous; glossy. Color: Apex: Close to 53B. Mid-section: Distally, close to 34B and proximally, close to 144C. Base: Close to 147C.

*Involucral bracts*.—Quantity per inflorescence: About 60 arranged in about four whorls. Length: About 1.1 cm. Width: About 4 mm. Shape: Narrowly ovate; mostly horizontal. Apex: Acute. Base: Cuneate. Margin: Entire. Texture and luster, upper surface: Sparsely pubescent; margins, moderately pubescent; slightly glossy. Texture and luster, lower surface: Sparsely pubescent; slightly glossy. Color, upper surface: Close to 138A; towards the margin, close to NN137B. Color, lower surface: Close to 138A; towards the margin, close to 137A.

*Peduncles*.—Length: About 13.1 cm. Diameter: About 4.5 cm. Strength: Strong. Aspect: Mostly upright. Texture: Moderately pubescent; strigose. Color: Close to a blend of 147A and 152A and covered with blotches of close to N186D.

*Reproductive organs*.—Androecium (present on ray and disc florets): Quantity per floret: Five. Filament length: About 5 mm. Filament color: Close to 145D. Anther length: About 3 mm. Anther shape: Lanceolate. Anther color: Close to a blend of N200A and 202A. Pollen amount: Moderate. Pollen color: Close to 17B. Gynoecium (present only on disc florets): Quantity per floret: One. Pistil length: About 9 mm. Stigma shape: Decurrent, unequal. Stigma color: Close to 173A. Style length: About 7 mm. Style color: Close to 145C. Ovary color: Close to 157B. Seeds and fruits: To date, seed and fruit development have not been observed on plants of the new *Echinacea*.

Pathogen & pest resistance: To date, plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35° C. and to be hardy to USDA Hardiness Zones 3 to 4.

It is claimed:

1. A new and distinct *Echinacea* plant named 'IFECSSPUR' as illustrated and described.

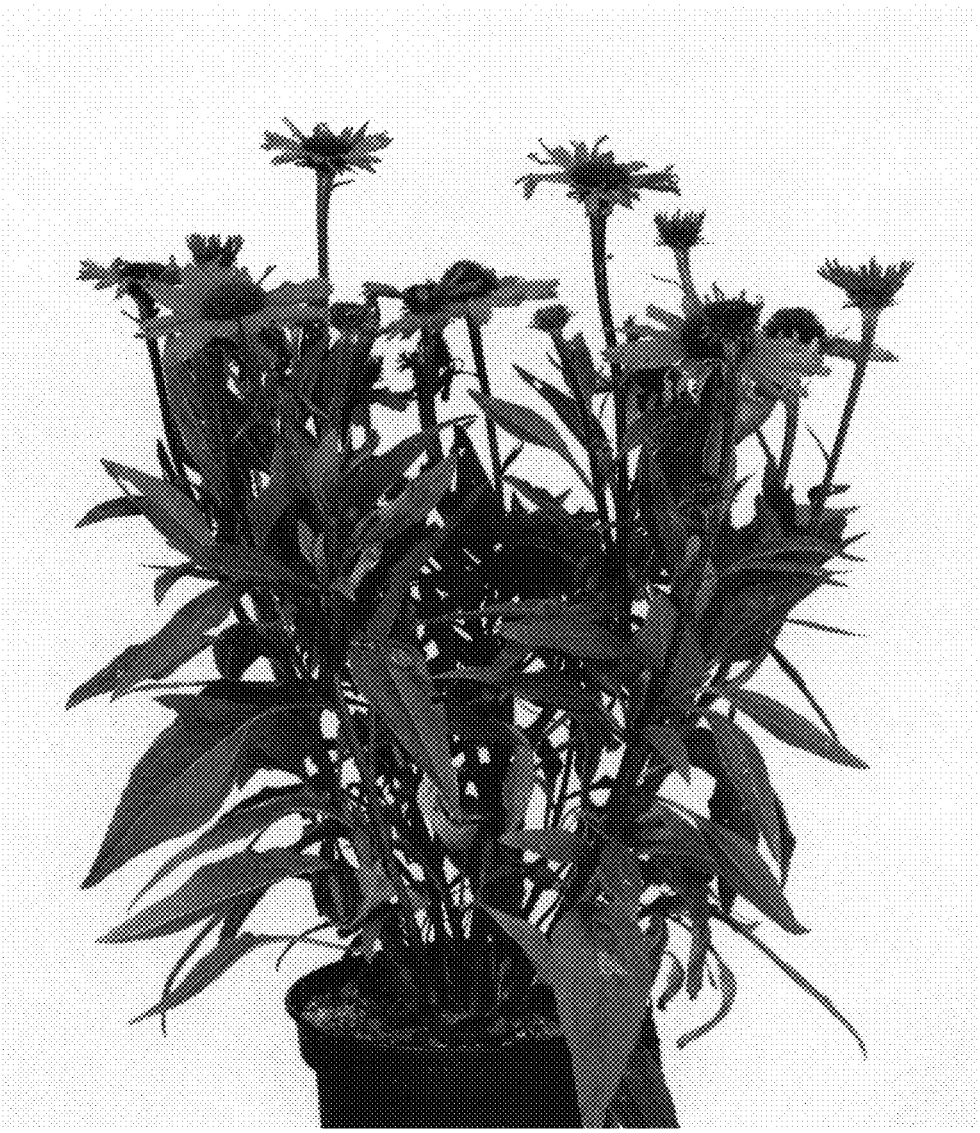

* * * * *